(12) United States Patent
Wick

(10) Patent No.: US 8,470,737 B2
(45) Date of Patent: Jun. 25, 2013

(54) COMPOSITION AND METHOD FOR TREATING INJURED WOODY PLANTS, BUSHES AND TREES

(75) Inventor: Patrick A. Wick, Farmington, PA (US)

(73) Assignee: Wicktek, Inc., Pittsburgh, PA (US)

( * ) Notice: Subject to any disclaimer, the term of this patent is extended or adjusted under 35 U.S.C. 154(b) by 271 days.

(21) Appl. No.: 12/925,999

(22) Filed: Nov. 4, 2010

(65) Prior Publication Data

US 2011/0111960 A1    May 12, 2011

Related U.S. Application Data

(60) Provisional application No. 61/280,595, filed on Nov. 6, 2009.

(51) Int. Cl.
| | |
|---|---|
| *A01N 59/00* | (2006.01) |
| *A01N 25/10* | (2006.01) |
| *A01N 25/02* | (2006.01) |
| *C09D 1/02* | (2006.01) |
| *C09J 1/02* | (2006.01) |
| *C04B 14/12* | (2006.01) |
| *C04B 16/08* | (2006.01) |
| *C04B 38/00* | (2006.01) |

(52) U.S. Cl.
USPC ........... 504/187; 504/360; 504/362; 106/600; 106/601

(58) Field of Classification Search
USPC ................... 106/600, 601; 504/187, 360, 362
See application file for complete search history.

(56) References Cited

U.S. PATENT DOCUMENTS 3,615,780 A * 10/1971 Kim et al. ..................... 106/608
3,706,581 A * 12/1972 Whitworth et al. ........... 405/264

OTHER PUBLICATIONS

McAvoy et al., "Silica Sprays Reduce the Incidence and Severity of Bract Necrosis in Poinsettia", 1996, HortScience, 31(7): 1146-1149.*

* cited by examiner

*Primary Examiner* — Jane C Oswecki
(74) *Attorney, Agent, or Firm* — Eckert Seamans Cherin & Mellott, LLC; Carol A. Marmo

(57) ABSTRACT

The invention relates to a composition and method for treating a wound site of a woody plant or tree. The composition includes about 70% to 90% water by volume of the total composition and about 10% to 30% sodium metasilicate by volume of the total composition. The method includes the steps of preparing the composition and applying the composition to form a coating on the wound site.

3 Claims, No Drawings

COMPOSITION AND METHOD FOR TREATING INJURED WOODY PLANTS, BUSHES AND TREES

CROSS-REFERENCE TO RELATED APPLICATIONS

This patent application claims the benefit of U.S. provisional patent application 61/280,595, filed on Nov. 6, 2009, the contents of which are incorporated herein by reference.

FIELD OF THE INVENTION

The invention relates to a composition and method for use in the preservation and healthful maintenance of woody plants and trees. In particular, the invention is useful to treat injury sustained by woody plants and trees.

BACKGROUND OF THE INVENTION

Typically, when a limb, branch or trunk of a tree or bush is cut or cracked, the tree or bush is injured. The injured tree or bush immediately begins a process of damage containment and repair of the injury. This process includes a collapse of the damaged cells at the cut surface in an effort to reduce "bleeding." Bleeding results in a loss of plant fluids as drying of the exposed surface commences.

Drying is not confined to the surface layer of cells at the cut. Often, cells located as deep as half an inch within the plant can experience fluid loss and drying. The resultant drying can permanently damage or kill the plant. A reduction in such drying is generally believed to be beneficial to the healing process by allowing the plant to maintain higher moisture levels at the wound site and prevent such cells from dying. Such cells can then continue to grow and form callus tissue over the surface of the wound. Thus, there is a need in the art to provide a means to prevent or stop drying at the site of the wound.

Various compounds and mixtures have been used on tree and bush wounds to prevent drying and promote healing. Most of these are based on paint, shellac or asphalt-derived compounds. These compounds have generally been found to actually retard the healing process.

Thus, there is an unmet need for a composition and method which is easy to apply to a wound site of a tree or bush (e.g., a tree bandage) and is effective for both reducing drying and die-back at a wound site.

BRIEF SUMMARY OF THE INVENTION

In one aspect, the invention provides a composition including about 70% to 90% water by volume of the total composition and about 10% to 30% sodium metasilicate by volume of the total composition.

In another aspect, the invention provides a method of making a composition including the steps of mixing together about 70% to 90% water and about 10% to 30% sodium metasilicate under conditions of constant temperature to produce a substantially homogeneous blend.

In yet another aspect, the invention provides a method of sealing a wound site of a tree, woody plant or bushy, including the steps of preparing a composition including about 70% to 90% by volume of water and about 10% to 30% by volume of sodium metasilicate, and applying the composition to the wound site to form a coating thereon.

DETAILED DESCRIPTION OF THE INVENTION

The invention includes a composition which can be applied to a damaged or cut section of a woody plant, bush or tree. For ease of description, the term "tree(s)" is used herein and, it is contemplated and understood that this term encompasses woody plant(s) and bush(es). When applied to the surface of the damaged or cut section, the invention seals (bandages) the wound in a manner that combines the composition with materials that are naturally part of the plant or tree itself to facilitate healing and to prevent further "bleeding". Further, the composition is a zero VOC (volatile organic compound) and therefore, it is easy and safe to use.

Various compounds and mixtures are known in the art and have been used on tree and bush wounds to prevent drying and promote healing. Most of these compounds are based on paint, shellac or asphalt-derived compounds. These compounds have generally been found to actually retard the healing process and can be toxic to humans. In contrast, the composition of the invention is non-toxic and environmentally safe.

The composition of the invention includes water ($H_2O$) and sodium metasilicate ($Na_2SiO_3$) to form an aqueous solution. The water is present in an amount of from about 70% to 90% by volume percent and the sodium metasilicate is present in an amount of from about 10% to 30% by volume percent. In an embodiment, the sodium metasilicate is in the form of an aqueous solution. The resulting blend is nearly odorless and opaque in color such that it is easy to apply to the wound by conventional methods, such as brushing or spraying.

The method of the invention includes mixing together about 70% to 90% water ($H_2O$) and 10% to 30% sodium metasilicate ($Na_2SiO_3$) under conditions of constant temperature to produce a substantially homogeneous blend. Further, the method includes applying, e.g., by brushing or spraying, this substantially homogeneous blend to a wound site of a woody plant or tree to form a coating thereon. The wound site can be the result of an injury or cutting, e.g., pruning to form a pruning site. The thickness of the coating is approximately 0.05 cm to 0.1 cm.

The method of the invention further includes allowing the coating to dry.

When the water and sodium metasilicate composition is applied to a tree wound, the composition chemically separates to form silicon dioxide ($SiO_2$). The sodium combines with available chlorine, which is naturally occurring in woody plants as a result of photosynthesis, to form halite (NaCl), a type of salt. Thus, the coating formed by the composition includes silicon dioxide which is a type of quartz or glass-like material that seals the pores and protects the wound while allowing the tree to form a callus over the wound.

I claim:

1. A method of sealing a wound site of a tree, woody plant or bush, comprising:
   preparing a composition comprising about 70% to 90% by volume of water and about 10% to 30% by volume of sodium metasilicate; and
   applying said composition to the wound site to form a coating thereon,
   wherein the wound site includes a cut or crack in the surface of a limb, branch or trunk of the tree, woody plant or bush.

2. The method of claim 1, wherein said coating is approximately 0.05 cm to 0.1 cm thick.

3. The method of claim 1, further comprising:
   drying said coating.

* * * * *